United States Patent [19]
Wagner et al.

[11] Patent Number: 5,387,699
[45] Date of Patent: Feb. 7, 1995

[54] PROCESS FOR PREPARING PYROMELLITIC DIANHYDRIDE

[75] Inventors: Werner Wagner, Munich; Frank Müller, Inning-Bachern; Hans-Jürgen Eberle, Munich; Franz Grundei, Ebersberg, all of Germany

[73] Assignee: Industrie GmbH, Munich, Germany

[21] Appl. No.: 171,813

[22] Filed: Dec. 22, 1993

[30] Foreign Application Priority Data

Feb. 25, 1993 [DE] Germany ............... 4305817

[51] Int. Cl.$^6$ ............... C07D 493/00; C07C 51/16
[52] U.S. Cl. ............... 549/239; 562/410; 562/412; 562/415
[58] Field of Search ............... 549/239; 562/410, 412, 562/415

[56] References Cited

U.S. PATENT DOCUMENTS

| | | | |
|---|---|---|---|
| 3,576,825 | 4/1971 | Bergman | 562/416 |
| 4,665,200 | 5/1987 | Nakanishi et al. | 549/239 |
| 4,719,311 | 1/1988 | Partonheimer | 562/413 |
| 4,824,992 | 4/1985 | Tanaka | 562/416 |
| 4,867,763 | 9/1989 | Scharf | 55/72 |

FOREIGN PATENT DOCUMENTS

| | | |
|---|---|---|
| 0169330 | 11/1950 | Austria . |
| 0405508 | 1/1979 | European Pat. Off. . |
| 0046397 | 2/1982 | European Pat. Off. . |
| 0330495 | 8/1985 | European Pat. Off. . |
| 0163231 | 12/1985 | European Pat. Off. . |
| 1943510 | 6/1970 | Germany . |
| 1468824 | 9/1973 | Germany . |
| 2422197 | 11/1974 | Germany . |
| 3734469 | 5/1988 | Germany . |
| 3730747 | 3/1989 | Germany . |
| 1282775 | 7/1972 | United Kingdom . |
| 1422308 | 1/1976 | United Kingdom . |

OTHER PUBLICATIONS

Chem. Systems Reports: PERP 1987-T-4, 16-40.
SRI International, PEP Report 466, 1989, 2-4 to 2-6.
Patent Abstracts of Japan 55-122787 (Sep. 1980).

*Primary Examiner*—Cecilia Tsang
*Attorney, Agent, or Firm*—Collard & Roe

[57] ABSTRACT

The invention relates to a process for preparing pyromellitic dianhydride (PMDA) by heterogeneously catalyzed oxidation in the gas phase by means of a gas containing molecular oxygen. The process involves oxidizing benzaldehydes which are 2,4,5-trialkylated by $C_1$- to $C_3$-alkyl groups or mixtures of benzaldehydes which are 2,4,5-trialkylated by $C_1$- to $C_3$-alkyl groups and benzenes which are 1,2,4,5-tetraalkylated by $C_1$- to $C_3$-alkyl groups in the presence of a catalyst. The catalyst contains as active components 5% to 95% by weight of one or more transition-metal oxides of sub-group IV of the Periodic Table of the Elements, from 1% to 50% by weight of one or more transition-metal oxides of sub-group V of the Periodic Table of the Elements. The catalyst also contains from 0% to 10% by weight of one or more oxides of elements of main group I of the Periodic Table of the Elements and/or from 0% to 50% by weight of one or more oxides of elements of main groups III, IV and V of the Periodic Table of the Elements and of elements of sub-groups VI and VII of the Periodic Table of the Elements. The indicated percentages by weight are based in each case on the total weight of the active components and add to 100% by weight.

13 Claims, No Drawings

PROCESS FOR PREPARING PYROMELLITIC DIANHYDRIDE

BACKGROUND OF THE INVENTION

1. Field of the Invention

The present invention relates to a process for preparing pyromellitic dianhydride (PMDA) by heterogeneously catalyzed oxidation in the gas phase by means of a gas containing molecular oxygen and to catalysts to be used in this process.

2. The Prior Art

PMDA has, up to now, been obtained on a large scale mainly by liquid-phase oxidation of 2,4,5-trimethylbenzaldehyde with atmospheric oxygen, in a process analogous to the process described in DE-A 1,943,510 (GB-A 1,282,775) for preparing terephthalic acid from p-toluylaldehyde, in which the pyromellitic acid thus obtained is dehydrated to PMDA. The 2,4,5-trimethylbenzaldehyde is prepared by carbonylation of 1,2,4-trimethylbenzene (pseudo-cumene) (DE-A 2,422,197 = GB-A 1,422,308). The use of acetic acid as a solvent and heavy-metal salts in combination with a bromide source (*Chem-Systems Report:* PERP 1987-T-4, 16–40) as catalysts necessitate, in this process, the use of high performance and therefore very expensive alloys (Hastelloy C) for the reactor. Besides the batchwise operation, a further disadvantage of this process is that the pyromellitic acid obtained by liquid-phase oxidation must be dehydrated to PMDA in a very energy-intensive step (>200° C.).

A further process for preparing PMDA employing the principle of liquid-phase oxidation is the Amoco process (U.S. Pat. No. 4,719,311). Using a similar catalyst (Co-Mn-Br), 1,2,4,5-tetramethylbenzene (durene) is oxidized with atmospheric oxygen to pyromellitic acid, which likewise still has to be dehydrated to PMDA. In addition to the disadvantages described for the above-mentioned process, this process has the further disadvantage that durene is above five times more expensive than pseudo-cumene.

A third PMDA process operates in the gas phase. Analogous to the oxidation of o-xylene to phthalic anhydride, durene is oxidized directly to PMDA over a heterogeneous catalyst in a multiple-tube reactor. U.S. Pat. No. 4,665,200 discloses $V_2O_5$, $TiO_2$, $P_2O_5$, $Nb_2O_5$, $Sb_2O_3$, $K_2O$ and $Cs_2O$ as catalyst components. Particular advantages of the gas-phase oxidation are continuous operation and the easy handling of the catalysts, as a result of which the use of expensive materials in plant construction can be dispensed with. In principle, it is possible to inexpensively retrofit existing plants for PMDA production. The energy-intensive dehydration of the liquid-phase process is eliminated, since the anhydride is desublimated directly from the reaction gas. A PMDA purity of 99% is achieved by means of suitable desublimation processes (DE-A 3,730,747 = U.S. Pat. No. 4,867,763).

A further way of obtaining PMDA from the reaction gas is gas scrubbing with an anhydrous solvent, a technology which is state of the art in, for example, the preparation of maleic anhydride (SRI International, PEP Report 46C, 1989). Further examples of the preparation of PMDA via gas-phase oxidation in the presence of vanadium- or titanium-containing catalysts are described in EP-A 405,508 and EP-A 330,195. A disadvantage of the gas-phase oxidation when compared with the previously known processes is the lower selectivity in comparison with liquid-phase oxidation.

For the gas-phase oxidation, starting materials which have been described are, in addition to 1,2,4,5-tetraalkylated benzenes, functionally substituted benzene derivatives which are prepared from trisubstituted benzenes, for example pseudo-cumene. Functional groups described are chloromethyl and alkoxymethyl (AT-PS 169 330). For ecological reasons, chlorine-containing aromatics are questionable, especially at such high reaction temperatures as occur in the gas-phase oxidation. Alkoxymethylbenzenes are likewise produced via a chloromethylation and are to be avoided for the same reason.

In summary, the most serious disadvantages of the processes known from the prior art are, for the liquid-phase oxidation processes, the expensive reactor materials because of the corrosive catalysts, the long downtimes as a result of batchwise operation, the energy-intensive dehydration of the acid to the anhydride and, for the gas-phase oxidation processes, their expensive raw material base and low selectivity.

SUMMARY OF THE INVENTION

It is an object of the present invention to provide a process which combines the advantages of the liquid-phase oxidation, namely the favorable raw material base, with the advantages of the gas-phase oxidation, namely economical reactor materials, continuous operation, avoidance of the dehydration step by desublimation of the anhydride, and, at the same time, gives the desired product with very high selectivity.

It has been found that especially the use of alkylated benzaldehydes in the gas-phase oxidation is particularly advantageous. In comparison with durene oxidation, aldehyde oxidation is substantially more selective, so that the PMDA yield increases. This was not to be expected since, at such high temperatures as occur in a gas-phase reactor, aromatic aldehydes very easily undergo decarbonylation or decomposition reactions and should therefore be unsuitable as starting materials for the gas-phase oxidation to PMDA. A further desirable effect is that the formation of by-products, particularly trimellitic anhydride (TMSA), is suppressed. Advantage can thus be taken of the price advantage of the pseudo-cumene base, since, in analogy with the first step of the liquid-phase oxidation, trimethylbenzaldehyde (TMBA) can be prepared relatively simply by carbonylating the inexpensive pseudo-cumene.

The invention provides a process for preparing pyromellitic dianhydride (PMDA) by heterogeneously catalyzed oxidation in the gas phase by means of a gas containing molecular oxygen, which comprises oxidizing benzaldehydes which are 2,4,5,-trialkylated by $C_1$- to $C_3$-alkyl groups or mixtures of benzaldehydes which are 2,4,5-trialkylated by $C_1$- to $C_3$-alkyl groups and benzenes which are 1,2,4,5-tetraalkylated by $C_1$- to $C_3$-alkyl groups in the presence of a catalyst which contains as active components 5% to 95% by weight of one or more transition-metal oxides of sub-group IV of the Periodic Table of the Elements, from 1% to 50% by weight of one or more transition-metal oxides of sub-group V of the Periodic Table of the Elements, from 0% to 10% by weight of one or more oxides of elements of main group I of the Periodic Table of the Elements and/or from 0% to 50% by weight of one or more oxides of elements of main groups III, IV and V of the Periodic Table of the Elements and of elements of sub-groups VI and VII of the Periodic Table of the Elements, where the indicated percentages by weight are based in each case on the total weight of the active components and add up to 100% by weight.

PMDA is obtained by catalytic gas-phase oxidation starting from 2,4,5-trialkylated benzaldehydes, in which the alkyl groups may be methyl, ethyl, propyl or isopropyl radicals, or starting from a mixture 2,4,5-trialkylated benzaldehydes, in which the alkyl groups may be methyl, ethyl, propyl or isopropyl radicals, and 1,2,4,5-tetraalkylated benzenes, in which the alkyl groups may likewise be methyl, ethyl, propyl or isopropyl radicals. If these mixtures are used, the weight ratio of 2,4,5-trialkylated benzaldehydes to 1,2,4,5-tetraalkylated benzenes is preferably from 10:1 to 1:10. Preferably, 2,4,5-trimethylbenzaldehyde or a mixture of 2,4,5-trimethylbenzaldehyde and 1,2,4,5-tetramethylbenzene (durene) is used. The particularly preferred starting material is 2,4,5-trimethylbenzaldehyde alone.

Preferably, the catalyst contains as active components from 10% to 90% by weight of an oxide of titanium and/or zirconium, from 5% to 35% by weight of an oxide of vanadium and/or niobium and also from 0% to 5% by weight of one or more oxides selected from the group consisting of oxide compounds of potassium, rubidium, cesium and/or from 0.1% to 10% by weight of one or more oxides selected from the group consisting of phosphorus, antimony, bismuth, chromium, molybdenum, tungsten, manganese, where the indicated percentages by weight are based in each case on the total weight of the active components.

Particularly preferred catalyst compositions have titanium dioxide as the oxide of the transition metals of sub-group IV of the Periodic Table of the Elements, vanadium pentoxide as the oxide of transition metals of sub-group V of the Periodic Table of the elements, which are doped with the phosphorus pentoxide, either alone or together with $Sb_2O_3$ and/or $Cs_2O$. The most preferred catalyst compositions are those containing titanium dioxide in the anatase form having a BET surface area of from 5 to 200 $m^2/g$.

The catalyst may be used as a solid catalyst (compacts, extrudates, granules) or in the form of catalysts being coated onto a substrate, the form depending on the gas-phase oxidation process. For example, in the fluidized-bed process, catalysts in granulated form are used and, in the fixed-bed process, compacts or rings or beads coated with the active catalyst components (coated catalysts) are used.

The fixed-bed process is preferred; for it the catalytically active composition is on inert support or substrate materials. The proportion of the active catalyst composition, based on the total weight, i.e., the sum of the weights of the support bodies and the active catalyst component composition, is from 1% to 30% by weight, preferably from 2% to 15% by weight. In principle, the substrate supports may be of any desired shape and surface structure. Preferred supports are, however, regularly shaped, mechanically stable bodies such as beads, rings, half rings, cylinders, saddles, having a smooth pore-free surface. The size of the support bodies is primarily determined by the dimension, particularly the internal diameter of the reaction tube, if the catalyst is used in a tube or multiple-tube reactor. The support diameter should then be between $\frac{1}{2}$ and 1/10 of the reactor internal diameter. Suitable inert materials for the supports are, for example, steatite, duranite, silicon carbide, earthenware, porcelain, silicon dioxide, silicates, aluminum oxide, aluminates or mixtures of these materials. Preferably, beads or rings of steatite are used.

The active components may be applied to the inert supports in conventional manner. Hence, the supports may be coated with an aqueous suspension of the mixture or else of the individual components in a rotating-tube furnace at 200°–300° C. The active components may be applied in the form of the oxides or in the form of compounds which are converted to the oxides under the conditions of the gas-phase oxidation or in a preceding heat-treatment step. Supported catalysts having coatings which adhere extremely well are obtained by applying to the support bodies an aqueous suspension which contains the mixture or the individual components and an organic binder. Such processes for coating catalysts onto supports are described, for example, in DE-B 2,106,796 (U.S. Pat. No. 3,799,886).

In the process according to the invention, the starting materials are reacted together with an oxygen-containing gas in the presence of the oxidation catalyst described above, preferably in fixed-bed reactors. Customary fixed-bed reactors are, for example, reaction tubes, which are combined to form a multiple-tube reactor and are surrounded by a heat-exchange medium. The reaction tubes are arranged vertically and the reaction mixture flows through them from the top to the bottom. They are made of a material which is inert to the heat-exchange medium, catalyst, starting materials and products. In general, they were made of a suitable steel, and have a length of from 2000 to 4000 mm, preferably from 2500 to 3500 mm, an internal diameter of from 10 to 30 mm, preferably from 18 to 26 mm, and a wall thickness of from 1 to 4 mm. Heat-exchange media which have proven suitable in industrial practice are eutectic salt mixtures, such as a chloride-free melt of potassium nitrate and sodium nitrite.

The catalyst is introduced into the reaction tubes from the top and fixed in place by securing devices fitted near the lower ends of the tubes. The bed depth may be between 900 and 3300 mm. The reaction tubes may, if required, be packed with layers of support bodies of varying shape and dimensions and varying concentration and composition of the active components.

In the process of the invention, the reaction gas containing 2,4,5-trialkylated benzaldehyde, which may be mixed with 1,2,4,5-tetraalkylated benzene, with an oxygen-containing gas, preferably air, is brought into contact with the catalyst. Preferably, the space velocities are from 800 to 8000 $h^{-1}$, particularly preferably from 1000 to 6000 $h^{-1}$. The mixing ratio is from 10 to 100 g of starting material/$Nm^3$, preferably from 10 to 40 g of starting material/$Nm^3$. The reaction temperature is from 250° to 600° C., preferably from 300° to 500° C.

After the reaction, the pyromellitic dianhydride (PMDA) formed is isolated from the reaction gas in a conventional manner by desublimation in a downstream separator at from 40° to 80° C. (DE-A 3,730,747 = U.S. Pat. No. 4,867,763) or by corresponding gas scrubbing with a suitable solvent.

The pyromellitic dianhydride obtainable from the process of the invention is used as starting material (comonomer) for producing high-temperature resistant polymers, as hardener for epoxy resins and as starting material for plasticizer components.

Other objects and features of the present invention will become apparent from the following detailed description considered in connection with the accompanying Examples, which disclose embodiments of the present invention. It should be understood, however, that the Examples are designed for the purpose of illustration only and not as a definition of the limits of the invention.

DETAILED DESCRIPTION OF PREFERRED EMBODIMENTS

Catalyst Preparation 55 g of $TiO_2$ (anatase), 7 g of $V_2O_5$ and 3.5 g of $(NH_4)_2HPO_4$ were suspended in 400 ml of deionized water and stirred for 18 hours, so as to obtain a homogeneous mixture. Before the mixture was applied to 1000 g of 8 mm steatite beads support, 20 g of a copolymer of vinyl acetate and vinyl laurate in the form of a 50% by weight aqueous dispersion were added to the suspension. Subsequently, the suspension was applied to the support with evaporation of the water. After a heat-treatment step of 4 hours at 410° C. and an air flow rate of 0.5 $Nm^3/h$, the catalytically active composition had a surface area of 95 $m^2/g$ (measured by BET).

All the examples below were carried out in a reaction tube reflecting an industrial scale. The length of the reaction tube was 3.3 m (bed depth 2.8 m, corresponding to 1730 g of catalyst), its diameter being 25 mm. The reactor was heated by a circulating salt bath (eutectic, chloride-free salt melt of potassium nitrate and sodium nitrite). The feed rate of air was 4 $Nm^3/h$. The mixing ratio of starting material/air was from 12 to 35 $g/Nm^3$ of air. The purity of the 2,4,5-trimethylbenzaldehyde was between 95% and 98% by weight. The purity of the 1,2,4,5-tetramethylbenzene (durene) in the comparative examples was from 97% to 99% by weight.

The reaction conditions and yields for the two examples and the two comparative examples are shown in the table below.

TABLE

|  | Example 1 | Example 2 | Comparative Example 1 | Comparative Example 2 |
| --- | --- | --- | --- | --- |
| Starting Material | TMBA | TMBA | Durene | Durene |
| SBT (°C.) | 375 | 380 | 370 | 375 |
| PMDA (% by weight*) | 83 | 90 | 75 | 75 |
| TMA (% by weight**) | 0.8 | 0.7 | 5 | 4 |

\* = based on 100% strength starting material
\*\* = based on PMDA
SBT = salt bath temperature
TMBA = 2,4,5-Trimethylbenzaldehyde
TMA = Trimellitic anhydride To enable the TMA content of the PMDA separated out to be analyzed, the reaction product was converted to the methyl ester with an $H_2SO_4/CH_3OH$ mixture (1:3 % by volume) and the TMA content subsequently determined by gas chromatography.

While only a single embodiment of the present invention has been shown and described, it is to be understood that many changes and modifications may be made thereunto without departing from the spirit and scope of the invention as defined in the appended claims.

What is claimed is:

1. A process for preparing pyromellitic dianhydride (PMDA) by heterogeneously catalyzed oxidation in the gas phase, comprising:
    contacting a reaction gas containing molecular oxygen and an aromatic reactant selected from the group consisting of benzaldehydes which are 2,4,5-trialkylated by alkyl groups having from 1 to 3 carbon atoms, and mixtures of benzaldehydes which are 2,4,5-trialkylated by alkyl groups having from 1 to 3 carbon atoms and benzenes which are 1,2,4,5-tetraalkylated by alkyl groups having from 1 to 3 carbon atoms;
    with an oxidation catalyst which contains as active catalyst components
    (a) from 5% to 95% by weight of one or more transition-metal oxides of sub-group IV of the Periodic Table of the Elements; and
    (b) from 1% to 50% by weight of one or more transition-metal oxides of sub-group V of the Periodic Table of the Elements; and
    (c) from 0% to 10% by weight of one or more oxides of elements of main group I of the Periodic Table of the Elements; and
    (d) from 0% to 50% by weight of one or more oxides of elements of main groups III, IV and V of the Periodic Table of the Elements and of elements of sub-groups VI and VII of the Periodic Table of the Elements;
    where the indicated percentages by weight are based in each case on the total weight of the active components and add up to 100% by weight.
2. The process as claimed in claim 1,
    wherein said aromatic reactant is 2,4,5-trimethylbenzaldehyde or a mixture of 2,4,5-trimethylbenzaldehyde and 1,2,4,5-tetramethylbenzene in a weight ratio of from 10:1 to 1:10.
3. The process as claimed in claim 1,
    wherein said oxidation is carried out in a fixed-bed reactor with air at space velocities of from 800 to 8000 $h^{-1}$, in a mixing ratio of from 10 to 100 g of starting material/$Nm^3$ and at reaction temperature of from 250° C. to 600° C.; and
    isolating the pyromellitic dianhydride (PMDA) from the reaction gas by desublimation in a downstream separator.
4. The process as claimed in claim 1,
    wherein said oxidation is carried out in a fixed-bed reactor with air at space velocities of from 800 to 8000 $h^{-1}$, in a mixing ratio of from 10 to 100 g of starting material/$Nm^3$ and at reaction temperature of from 250° C. to 600° C.; and
    isolating the pyromellitic dianhydride (PMDA) from the reaction gas by scrubbing the corresponding gas with a suitable solvent.
5. The process as claimed in claim 1, wherein the active catalyst components comprise:
    (a) from 10% to 90% by weight of one or more oxides selected from the group consisting of oxide compounds of titanium and zirconium; and
    (b) from 5% to 35% by weight of one or more oxides selected from the group consisting of oxide compounds of vanadium and niobium; and
    (c) from 0% to 5% by weight of one or more oxides selected from the group consisting of oxide compounds of potassium, rubidium and cesium; and
    (d) from 0.1% to 10% by weight of one or more oxides selected from the group consisting of oxide compounds of phosphorus, antimony, bismuth, chromium, molybdenum, tungsten and manganese;
    where the indicated percentages by weight are based in each case on the total weight of the active catalyst components.
6. The process as claimed in claim 1, further comprising support bodies for the active catalyst components; and wherein the proportion of the active catalyst components, based on the total weight of support bodies and active catalyst components, is from 1% to 30% by weight.

7. The process as claimed in claim 6, wherein the supports used are beads or rings.

8. The process as claimed in claim 1, wherein the active catalyst components are titanium dioxide in the anatase form having a BET surface area of from 5 to 200 m²/g, vanadium pentoxide and phosphorus pentoxide which optionally contains $Sb_2O_3$ or $Cs_2O$.

9. A process for preparing pyromellitic dianhydride (PMDA) by heterogeneously catalyzed oxidation in the gas phase, comprising:

contacting a reaction gas containing molecular oxygen and an aromatic reactant consisting of benzaldehydes which are 2,4,5-trialkylated by alkyl groups having from 1 to 3 carbon atoms;

with an oxidation catalyst which contains as active catalyst components (a) from 5% to 95% by weight of one or more transition-metal oxides of sub-group IV of the Periodic Table of the Elements; and (b) from 1% to 50% by weight of one or more transition-metal oxides of sub-group V of the Periodic Table of the Elements; and (c) from 0% to 10% by weight of one or more oxides of elements of main group I of the Periodic Table of the Elements; and (d) from 0% to 50% by weight of one or more oxides of elements of main groups III, IV and V of the Periodic Table of the Elements and of elements of sub-groups VI and VII of the Periodic Table of the Elements;

where the indicated percentages by weight are based in each case on the total weight of the active components and add up to 100% by weight.

10. The process as claimed in claim 9, wherein the active catalyst components comprise:

(a) from 10% to 90% by weight of one or more oxides selected from the group consisting of oxide compounds of titanium and zirconium; and (b) from 5% to 35% by weight of one or more oxides selected from the group consisting of oxide compounds of vanadium and niobium; and (c) from 0% to 5% by weight of one or more oxides selected from the group consisting of oxide compounds of potassium, rubidium and cesium; and (d) from 0.1% to 10% by weight of one or more oxides selected from the group consisting of oxide compounds of phosphorus, antimony, bismuth, chromium, molybdenum, tungsten and manganese;

where the indicated percentages by weight are based in each case on the total weight of the active catalyst components.

11. The process as claimed in claim 9, further comprising support bodies for the active catalyst components; and wherein the proportion of the active catalyst components, based on the total weight of support bodies and active catalyst components, is from 1% to 30% by weight.

12. The process as claimed in claim 11, wherein the supports used are beads or rings.

13. The process as claimed in claim 9, wherein the active catalyst components are titanium dioxide in the anatase form having a BET surface area of from 5 to 200 m²/g vanadium pentoxide and phosphorus pentoxide which optionally contains $Sb_2O_3$ or $Cs_2O$.

* * * * *